(12) United States Patent
Bazarov et al.

(10) Patent No.: US 6,571,634 B1
(45) Date of Patent: Jun. 3, 2003

(54) METHOD OF IN-TUBE ULTRASONIC INSPECTION

(75) Inventors: Alexandr J. Bazarov, Kolomna (RU);
Alexandr P. Desyatchikov, Kolomna
(RU); Denis A. Desyatchikov, Kolomna
(RU); Vladimir N. Eliseev, Kolomna
(RU); Mikhail A. Isupov, Kolomna
(RU); Nikolai A. Karasev, Kolomna
(RU); Sergei P. Kirichenko, Kolomna
(RU); Gennady A. Kornev, Kolomna
(RU); Nikolai V. Nikolaev, Kolomna
(RU); Andrei M. Slepov, Kolomna
(RU); Anatoly V. Smirnov, Kolomna
(RU); Sergei V. Chernov, Kolomna
(RU)

(73) Assignee: NGKS International Corp., Richmond Hill (CA)

( * ) Notice: Subject to any disclaimer, the term of this patent is extended or adjusted under 35 U.S.C. 154(b) by 0 days.

(21) Appl. No.: 10/231,725

(22) Filed: Aug. 30, 2002

(30) Foreign Application Priority Data

Dec. 25, 2001 (RU) ......................................... 2001134936

(51) Int. Cl.⁷ ............................................... G01N 29/04
(52) U.S. Cl. ...................................................... 73/623
(58) Field of Search ...................... 73/623, 622, 1.82, 73/1.83, 602, 609, 629, 631

(56) References Cited

U.S. PATENT DOCUMENTS

| | | | |
|---|---|---|---|
| 4,056,971 A | * | 11/1977 | van Valkenburg et al. .... 73/629 |
| 4,162,635 A | | 7/1979 | Triplett et al. |
| 4,909,091 A | | 3/1990 | Ellmann et al. |
| 5,062,300 A | | 11/1991 | Vallee |
| 5,460,046 A | | 10/1995 | Maltby et al. |
| 5,497,661 A | | 3/1996 | Stripf et al. |
| 5,635,645 A | | 6/1997 | Ottes et al. |

FOREIGN PATENT DOCUMENTS

| | | |
|---|---|---|
| EP | 0 271 670 B2 | 6/1988 |
| EP | 0 304 053 B1 | 2/1989 |
| EP | 0 561 867 B1 | 9/1993 |
| EP | 0 616 692 B1 | 9/1994 |
| RU | 2018817 C1 | 8/1994 |
| RU | 2042946 C1 | 8/1995 |
| RU | 2108569 C1 | 4/1998 |
| WO | WO 96/13720 A1 | 5/1996 |

* cited by examiner

Primary Examiner—Helen Kwok
Assistant Examiner—Tamiko Bellamy
(74) Attorney, Agent, or Firm—Quarles & Brady LLP (57) ABSTRACT

A method of in-tube ultrasonic inspection of pipelines is carried out by passing inside the pipeline a scanning pig, emitting ultrasonic probing pulses towards the pipe wall and receiving the reflected ultrasonic pulses. The received pulses are amplified using an amplification factor which is increased depending on the time elapsed from the moment of emitting the probing pulse. The threshold values of the pulse amplitudes are also varied depending on time. Digital values of the pulse amplitudes and the time elapsed from the moment of emitting the probing pulse and corresponding to each value of the amplitude are obtained. The method allows for compensation for the effect of ultrasound attenuation in the material on the amplitudes of the reflected pulses and, in this manner, to increase the accuracy of determining the geometrical parameters of the flaws, a probability of their detection and efficiency of estimation of their danger.

13 Claims, 5 Drawing Sheets

METHOD OF IN-TUBE ULTRASONIC INSPECTION

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

This invention relates to methods of ultrasonic inspection of long-distance pipelines, mainly trunk oil pipelines, oil-products pipelines and gas pipelines, while providing acoustic communication between the ultrasonic sensors and the pipe walls (for example, with the help a so-called "pig" or a scanning device which is put into the pipeline and transported under power of the fluid flow in the pipeline). The inspection pig has built-in sensors, means for measurement, conversion and recording of the measured data and a device for collecting the digital data in the process of pig travel and for processing the obtained data to detect the flaws in the pipe walls and to determine the parameters of the detected flaws, as well as their location in the pipeline.

2. Description of the Related Art

Known in the art is a method of in-tube ultrasonic inspection [RU2042946, RU2108569, U.S. Pat. No. 4,162,635] effected by passing inside a pipeline a scanning pig having ultrasonic sensors, measuring means for measurement, processing and storage of the measured data. During the pig travel ultrasonic probing pulses are emitted towards the walls and the respective reflected ultrasonic pulses are received.

Also known in the art is a method of in-tube ultrasonic inspection [WO96/13720 (relevant patent documents: U.S. Pat. No. 5,587,534, CA2179902, EP0741866, AU4234596, JP3058352), EP0304053, (relevant patent documents: U.S. Pat. No. 4,964,059, CA1292306, NO304398, JP1050903), U.S. Pat. No. 5,062,300 (relevant patent documents: CA1301299, EP0318387, DE3864497, FR2623626, JP2002923), U.S. Pat. No. 5,460,046, (relevant patent documents: EP0684446, JP7318336), EP0271670 (relevant patent documents: U.S. Pat. No. 4,909,091, CA1303722, DE3638936, NO302322, JP63221240), EP0616692, (relevant patent documents: WO9312420 U.S. Pat. No. 5,635,645, CA2125565, DE4141123, JP2695702)] by passing inside the pipeline a scanning pig accommodating ultrasonic sensors, means for measurement, processing and storage of the measured data, and by emitting ultrasonic probing pulses during the pig travel and receiving the ultrasonic pulses reflected from the internal and external walls of the pipeline, the run time of the above pulses being measured.

These methods allow one to find out corrosive flaws such as loss of metal and scaling and to determine the parameters of these flaws. However, to detect crack-like damage of the pipe wall and to determine their depth, one needs information on the amplitudes of the received pulses. The absence of such an information in the above methods does not allow one to use these methods for crack detection.

Known in the art is a method of in-tube ultrasonic inspection of pipelines [RU2018817] effected by passing inside the pipeline a scanning pig carrying ultrasonic sensors, means for measurement, processing and storage of the measured data, emission of ultrasonic probing pulses during the pig travel and reception of the reflected ultrasonic pulses corresponding to the probing pulses with the help of said ultrasonic sensors, amplifying the output electric pulses of the sensors corresponding to the received ultrasonic pulses, converting and storing the measured data.

This method is characterized in that a mirror ultrasonic pulse is separated from the received ultrasonic pulses depending on the arrival time, the electric pulses corresponding to the separated mirror ultrasonic pulses are converted into a control voltage depending on the amplitude of the mirror pulse, and the control voltage is used to control the amplification of the pulses reflected from the flaws.

An advantage of this method is that it allows one to correct the errors when measuring the amplitudes of the pulses arising due to the acoustic attenuation in the depositions on the inner wall of the pipeline, the thickness of these depositions being different in the different sections of the pipeline.

The main disadvantage of the above method is that the method is practically inapplicable for reception of ultrasonic pulses subjected to multiple reflections because it is practically impossible to separate "on-line" mirror pulses with preset parameters among all repeatedly reflected ultrasonic pulses for generating a control voltage. Besides, in the given method no account is taken for the attenuation of the ultrasonic pulses in the pipe wall and the losses due to the partial penetrability of the media interface during the multiple reflections in the pipe wall.

The prior art of the proposed invention is a method of in-tube ultrasonic inspection of pipelines [U.S. Pat. No. 5,497,661 (relevant patent documents: WO9210746, EP0561867, CA2098480 DE4040190)] by passing inside the pipeline a scanning pig comprising ultrasonic sensors, means for measurement, processing and storage of the measured data, including the steps of emission of ultrasonic probing pulses during the pig travel and reception of the reflected ultrasonic pulses corresponding to the probing pulses, using the same ultrasonic sensors, amplification of the electric pulses from the sensors, corresponding to the received ultrasonic pulses, conversion and storage of the measured data.

This method is characterized in that it includes reception of at least one ultrasonic pulse reflected from the inner wall of the pipeline and at least two ultrasonic pulses reflected from the external wall of the pipeline, the reflected pulses being picked up by at least one ultrasonic sensor and amplified.

To receive the pulses after emitting the probing pulse, a time window is created having such a width that the pulse reflected from the inner wall of the pipeline and the two pulses reflected from the external wall of the pipeline are within the window, the received pulses being digitized.

The digitized pulses are filtered and parametrized. The maximum time and amplitude are determined for each reflected pulse and compared with a digital threshold value.

The width and amplitude of the reflected filtered and parametrized pulses are sent to a computer module, in which the parametrized pulses are processed to determine the time between the arrival of the nearest pulse reflected from the external wall of the pipeline and the arrival of the pulse reflected from the inner wall thereof. The parametrized pulse whose amplitude is higher than or equal to the amplitude of the previous pulse is recorded.

The time of the pulse generation and the time of its run in the pipe wall are determined and recorded if the time slot between the ultrasonic pulse reflected from the pipeline inner wall and the first pulse reflected from the pipeline external wall coincides within an allowable limit with the time slot between the first and second pulses reflected from the external wall of the pipeline. In so doing all parametrized pulses, for which said time slots do not coincide within the allowable limit are recorded.

In this method both the time from the moment of emission of the probing pulse to the moment of reception of the reflected pulses and the amplitude of the reflected pulses are measured and this is a necessary condition for detection of cracks in the pipe wall. However, the crack detection is effected using ultrasonic pulses emitted at some angle (about 17°) to the normal of the inner wall of the pipeline and reflected from the crack forming a corner reflector with the internal or external wall of the pipeline. In this case, a crack-like flaw corresponds to one reflected ultrasonic pulse, and the application in the prior art condition of coincidence of the time slots between the multiple reflected pulses is inefficient. Besides, the amplitudes of the multiple reflected ultrasonic pulses decrease depending on the total thickness of the metal layer penetrated by the pulse and on the amount of reflections from the media interfaces.

An advantage of the prior art method is that the digital threshold value is varied depending on the result of selection of the pulses on the basis of a preset threshold value. However, for all reflected pulses corresponding to one ultrasonic probing pulse only one digital threshold value is set, i.e. a single threshold value for pulses with different amplitudes during the time of reception of the pulses corresponding to one probing pulse. As a results, the preset threshold value is undervalued for the first pulse (with a high amplitude) and is overvalued for the last pulse (with a low amplitude).

Furthermore, when testing a pipeline including pipes with a different wall thickness, the flaws having the width correspond to the pulses with different maximum amplitudes, the obtained data on the flaw width and, respectively, on its danger is unreliable.

Thus, there is a need for an improved method of in-tube ultrasonic inspection of pipelines.

SUMMARY OF THE INVENTION

A method according to the invention for in-tube ultrasonic inspection of pipelines can also be realized by passing inside the pipeline a scanning pig having ultrasonic sensors, means for measurement, processing and storage of the measured data; during the pig travel said method provides emission of ultrasonic probing pulses and reception of the reflected ultrasonic pulses corresponding to said probing pulses with the help of said ultrasonic sensors; amplification of the electric pulses fed from the sensors and corresponding to the received ultrasonic pulses; conversion and storage of the measured data; the amplitudes of the received electric pulses corresponding to the reflected ultrasonic pulses are compared with a preset threshold value, the time elapsed from the moment of emission of the ultrasonic probing pulse being determined in the process of measurement.

The present method differs from prior art methods in that within a selected time interval the amplification of the electric pulses from the ultrasonic sensors and the threshold value are varied discretely as preset functions of time, the dependencies of the amplifications factors and threshold values on time are read out during the scanning pig travel inside the pipeline from the device of conversion and storage of digital data while establishing individual dependence of the amplification factor and threshold value on time for each sensor simultaneously when the ultrasonic pulses are being received by this sensor.

The basic technical result obtained due to the realization of the invention is better probability of detection of flaws, especially crack-like flaws, when testing the pipelines including pipes having essentially different thickness of the walls and/or different properties of the pipe material, and a higher accuracy of determining the flaw size.

The mechanisms of achievement of this technical result consists in that a time-depending control of the amplification factor allows one to use the maximum accessible range of the analog-to-digital conversion (ADC) both for the pulses having passed a low thickness in the wall (at a small number of reflections or in a thin-walled pipe) and for the pulses having passed a larger thickness in the wall (at a great number of reflections or a thick-walled pipe) and to adjust the digital threshold value depending on the number of multiple reflections of the ultrasonic pulse and taking into account the periodic increase of the noise level depending on time elapsed from the moment of emission of the probing pulse.

In the process of searching crack-like flaws, the method allows one to use hardware to normalize the amplitude of the electric pulses corresponding to reflected ultrasonic pulses. The normalized amplitude of the ultrasonic pulses reflected from the crack-like flaws, to some extent, unambiguously corresponds to the depth of the crack or another flaw, and such hardware normalization allows one to realize the algorithms of the express analysis of the danger of the flaws under field conditions after completing the pig travel.

The amplification factor is discretely varied with a period of 2 to 20 microseconds and at a maximum step of 0.25 of the initial value of the amplification factor.

The threshold value is set up discretely with a period of 1 to 10 microseconds.

The lower limit of the above time interval is 3–20 microseconds and the upper limit of the interval is 40–200 microseconds.

The realization of the present method allows one to organize digital control of the dependence of the amplification factor and threshold value on time arbitrarily both before starting the scanning pig and during the pig travel inside the pipeline. The method can also be used for determining damage such as loss of metal by recording the multiple reflected ultrasonic pulses, as well as for detecting crack-like flaws.

The amplification factor K of the electric pulses from the ultrasonic sensors is increased depending on the time t elapsed from the moment of emission of the ultrasonic probing pulse, according to the function $K=c+a*(t-b)^n$ with a positive value "a", a value "n" not less than 1 and value "b" not exceeding the above-mentioned lower limit of the time interval; c is any appropriate value. In the preferred embodiment of the method, n=2.

In another embodiment, the amplification factor K of the electric pulses from the ultrasonic sensors is increased stepwise depending on the time elapsed from the moment of emission of the ultrasonic probing pulse characterized by the number of the step M, maximum number of steps N, and the initial value of the amplification factor $K_0$ according to the function $K=K_0*(1+a*2^{M-N})$ with a positive value "a" and a value "N" not less than 6. In the preferred embodiment of the method, N=8.

The above dependencies approximate empirical dependence for the attenuation of the ultrasound energy in medium being transported, deposits, material of the pipe wall in the working time interval of reception of ultrasonic pulses.

The amplification factor is controlled by periodically varying the noise level of the electronic circuits depending on time. The variation of the threshold value depending on time allows one to control the conditions of recording the received reflected ultrasonic pulses for each instant of time separately.

The dependence of the threshold value on time is set as a function of number of false pulses for some preset time interval exceeding the preset threshold value.

The false pulses are noise pulses.

Owing to the fact that the plurality of pipes constituting the pipeline being tested can include a considerable number of pipes made of a material whose acoustical absorption properties differ from those of the other pipes, and that the noise level of the electronic channels is a parameter depending both on the type of the ultrasonic sensors and on the individual properties of the sensors of the same type, the preliminarily selected dependence of threshold value on time is corrected depending on the efficiency of reducing the amount of data to be recorded. Such a progressive approximation allows one to adjust the efficiency of recording the useful pulses (corresponding to the reflected ultrasonic pulses) by preset criteria.

The false pulses are presented both by noise pulses and ultrasonic pulses reflected from the structural elements of the pig housings and sensor holders. As the number of such reflected pulses is low, the interpretation of the data effected after completing the scanning pig run enables the operator to uniquely identify such pulses.

The dependence of the threshold value on time is established in such a way that one probing pulse corresponds to 8–16 received false pulses exceeding the threshold value.

The application of the present method has shown that the above criteria are optimum for preventing the loss of useful pulses below the threshold and for avoiding overload of the electronics by processing the false pulses.

In one of the embodiments of the method, the number of false pulses, determined after completing the pipeline inspection by the pig, the dependence of the threshold value on time is set up for the subsequent diagnostic pig travel.

The analysis of the efficiency of application of thresholds for different sections of the main pipeline allows one to separate the effect of variation of the parameters of the electronics and a change of the type of pipes at different sections in the process of motion of the pig in the pipeline and to apply the most effective dependence for the subsequent diagnostic pig travel through the pipeline.

The above mentioned time interval is divided into some temporary zones, the scheme of division into temporary zones is used after each probing pulse, the false pulses are counted up in each zone, the threshold value for each zone is set depending on the number of false pulses exceeding the threshold in the respective zone for several probing pulses. A preferred number of temporary zones is not less than 4 and not more than 128. The temporary zones provide adjustment of the temporary dependence of threshold. A low number of zones provides coarse adjustment of the threshold. A large number of zones (fine division) allows one to adjust the threshold more precisely depending on time. The maximum amount of temporary zones is limited by the pulse duration.

The dependencies of the amplification factor and threshold value are established depending on the fluid medium being transported, when testing the pipeline, the passed distance and the pipe wall thickness. The initial values of the amplification factor are determined for each ultrasonic sensor before emitting the ultrasonic pulses to the wall of the tested pipeline by triggering the ultrasonic sensor by an electric pulse with preset parameters, thus forcing the sensor to emit an ultrasonic pulse perpendicularly to the nearest surface of an object of a known thickness and by receiving a respective ultrasonic pulse reflected from the remote surface of the object with the help of the same ultrasonic sensor while varying the amplification factor according to the algorithm realized by the data conversion and storage means to obtain a pulse with a maximum amplitude of the pulse. The code corresponding to the initial value of the amplification factor determined in this way is recorded in the digital data conversion and storage device. The lower limit of this range is at least 0.7 maximum allowable amplitude of the pulse, the upper limit being 0.8 maximum allowable amplitude of the pulse. In the present method, the digitized amplitude values of the received electric pulses are compared to the digital threshold value. The realization of the above algorithm allows automatic determination of the initial values of the amplification factor immediately before starting the scanning pig and during the pig travel (with metering the pipeline thickness).

In the preferred embodiment of the method, the amplitude of the noise pulse is measured at the absence of the probing and reflected ultrasonic pulses; the range of the analog-to-digital conversion of the amplitude values of the electric pulses corresponding to the received ultrasonic pulses are set as a function of the measured amplitude of the noise pulse; the amplified electric pulses corresponding to the received ultrasonic pulses are applied to one of the inputs of an adder; from the adder output the pulses are applied to the input of an analog-to-digital converter, and applied to the second input of the adder is a voltage from the digital-to-analog converter, said voltage depending on the measured amplitude of the noise pulse; another voltage is applied to the second input of the adder through a low-pass filter, the range limits are set depending on the number of discrete values; the range limits are set depending on the noise pulse level.

These operations allow one to use the maximum range of the ADC by removing the pulses corresponding to the noise of the electronic channels from the analog-to-digital converter.

The digitized parameters of the received pulses (corresponding to the probing pulses for each ultrasonic sensor are combined into data frames (for a group of sensors); The above parameters of the received pulses include digitized amplitudes of the pulses and time elapsed after emitting the respective probing pulse for each peak value. In the preferred embodiment, the alternative parameters of the received pulses include digitized peak amplitudes of the pulses and the time corresponding to the peak amplitude after emitting the respective probing pulse. An embodiment is preferable, in which one of the data frame includes the above parameters of the received pulses corresponding to 10–1000 probing pulses for each sensor of the group of ultrasonic sensors, for each said group of sensors a value of time is recorded, which is determined by a timer installed in the scanning pig, this time being uniquely matched with the time of triggering each sensor of the group. The digital data are recorded in the digital data storage device as a file of a plurality (100–10000) of data frames, as well as the time of opening and closing the file according to the clock of the computer controlling the data storage in a storage device. The computer clock time and the timer time are synchronized with each other and with the time of another timer located beyond the scanning pig. The above form of data recording allows one to uniquely determine the time of measurement of the data in case of distortion of some data in the process of conversion, recording, storage or reading and to find the reason of any malfunction.

These and other features, aspects, and advantages of the present invention will become better understood upon consideration of the following detailed description, drawings, and appended claims.

DETAILED DESCRIPTION OF THE INVENTION

Having solved the problem of increasing the reliability of in-tube inspection of main pipelines, we have developed in-tube ultrasonic defectoscopes (in-tube scanning pigs) for testing oil pipelines, gas pipelines, condensate pipelines, oil-products pipelines with a nominal diameter of 10" to 56". The scanning pigs of a preferred embodiment withstand the pressure of the pumped fluid medium of up to 80 standard atmospheres, have a flow rate of about 85% of the rated diameter of the pipeline, operate at a temperature of the pumped medium from 0° to +70° C., a minimum passable radius of turn of about 1.5 diameter of the pipeline. The pigs have different kinds of explosion protection such as an explosion-proof shell, an intrinsically safe electric circuit, a special explosion-proof finish with a current consumption of the scanning pig not higher than 9A.

Figure 1:
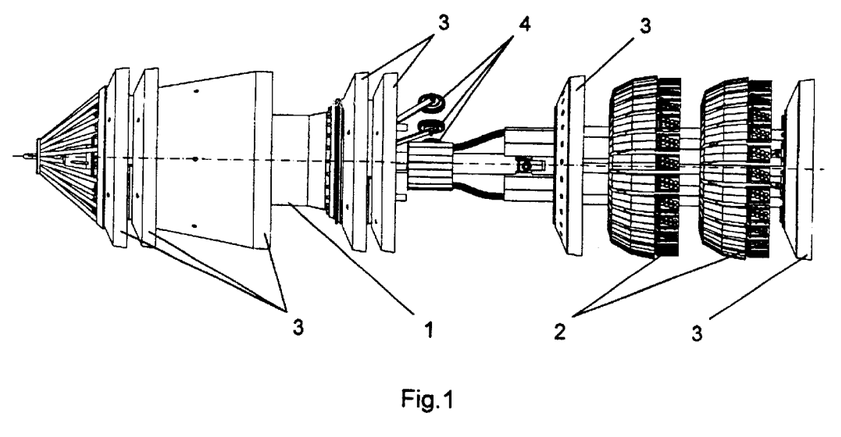
FIG. 1 illustrates one embodiment of the in-tube ultrasonic defectoscope.

One embodiment of the in-tube ultrasonic defectoscope for checking a pipeline with a diameter of 38" to 56" having a wall thickness of 4–30 millimeters is shown in FIG. 1. The pig comprises the following components: a body 1 forming a waterproof shell accommodating a power source and an electronic equipment for measuring, processing and storage of the obtained measured data on the basis of an onboard computer controlling the operation of the scanning pig during its travel inside the pipeline. The power source consists of storage batteries or galvanic cells with a total capacity of up to 1000 ampere-hours.

Mounted in the tailpiece of the pig are ultrasonic sensors 2 alternately emitting and receiving ultrasonic pulses. The polyurethane sealing rings 3 mounted on the pig body provide its positioning in the center of the pipeline and its motion with the current of the fluid medium pumped through the pipeline. The wheels of the odometers 4 mounted on the defectoscope body are pressed to the inner wall of the pipeline. During the pig motion the odometers generate pulses whose quantity is proportional to the distance measured by the odometer, the pulses from the odometers are processed in an electronic circuit providing matching of the time of triggering the ultrasonic sensors with the readings of the odometers, the information on the pig path measured by the odometers is recorded in a storage device of the onboard computer and, after completion of the diagnostic pig travel and processing of the stored data, allows one to determine the position of the flaws in the pipeline and, respectively, the place of subsequent excavation and repair of the pipeline.

The scanning pig is placed in the pipeline and the product (oil, condensate) is pumped through the pipeline. When the ultrasonic defectoscope travels inside the pipe, the ultrasonic sensors periodically emit acoustic pulses.

Figure 2:
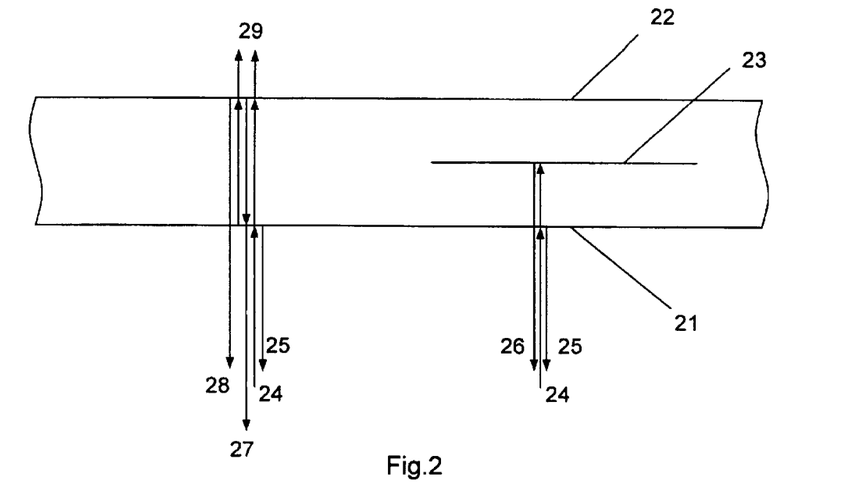
FIG. 2 is a diagram illustrating the path of the ultrasonic probing pulses emitted in a direction normal to the inner wall of the pipeline.

To accomplish the task of measuring the wall thickness, the ultrasonic pulses 24 of FIG. 2 are emitted perpendicularly to the internal surface of the pipeline. These pulses are partially reflected from the inner wall of the pipeline 21, from the external wall of the pipeline 22 or from the flaw area 23, for example, delaminated metal in the pipe wall. The ultrasonic pulses 29 partially pass through the media interface formed by the external wall of the pipeline.

Having emitted the ultrasonic pulses, the ultrasonic sensors start receiving pulses 25 reflected from the inner wall, pulses 27, 28 reflected from the external wall or pulses 26 reflected from the above-mentioned wall flaw.

Figure 3:
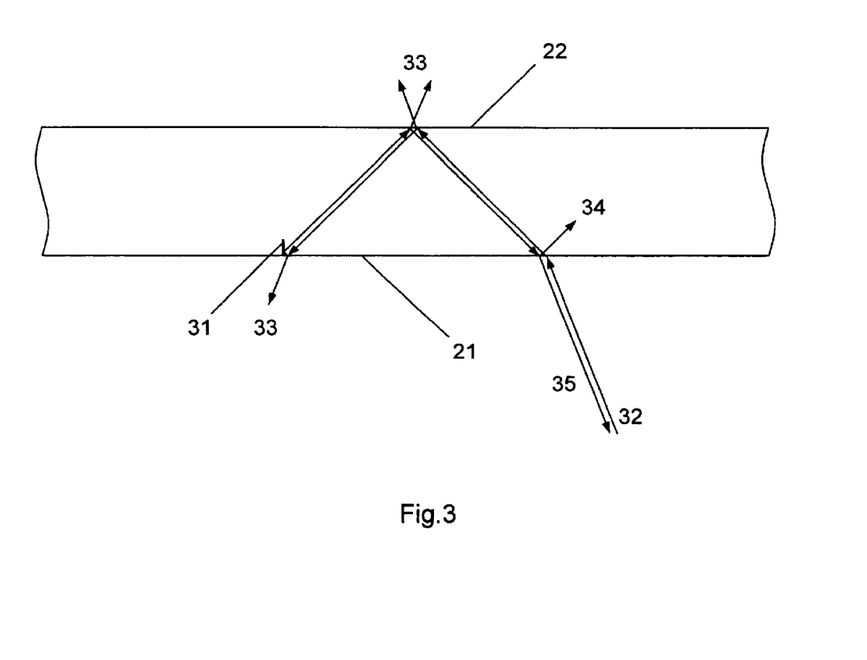
FIG. 3 is a diagram illustrating the path of the ultrasonic probing pulses emitted at an angle to the inner wall of the pipeline.

In order to detect cracks in the pipe wall, the ultrasonic pulses 32, FIG. 3, are emitted at an angle of about 15°–21° (preferably 17°–19°) to the inner surface of the pipe. The above pulses are partially reflected from the inner wall 21, from the external wall 22 or from the crack-like flaw 31. The ultrasonic pulses 33 partially pass through the media interface or are reflected (34) thus attenuating the useful reflected pulse 35.

Having emitted the ultrasonic pulses, the ultrasonic sensors switch to reception of the reflected pulses and receive pulses 35 reflected from the crack-like flaw 31.

Figure 4:
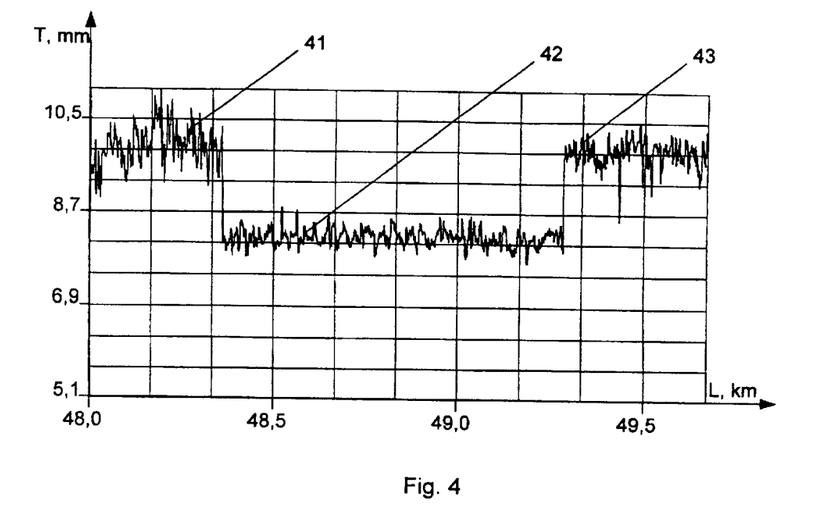
FIG. 4 illustrates the dependence of the wall thickness measured with the help of the scanning pig on the distance passed inside the pipeline being checked.

FIG. 4 illustrates the dependence of the wall thickness of the pipeline on the pipeline length. The sections 41, 42 and 43 in FIG. 4 correspond to the sections of the pipeline consisting of pipes having different nominal wall thickness: 10 millimeters for the section 41, 8.2 millimeters for the section 42 and 10 millimeters for the section 43. In this case, the difference in the nominal thickness is about 20% and therefore, the ultrasonic pulses reflected from the flaw in the pipe wall of a lower thickness are subjected to smaller attenuation than the pulses reflected from the flaw of the pipe wall of a greater thickness. At a fixed value of the amplification factor, the flaws with identical geometrical parameters in the walls of different thickness would correspond to different amplitudes of the received pulses.

Figure 6:
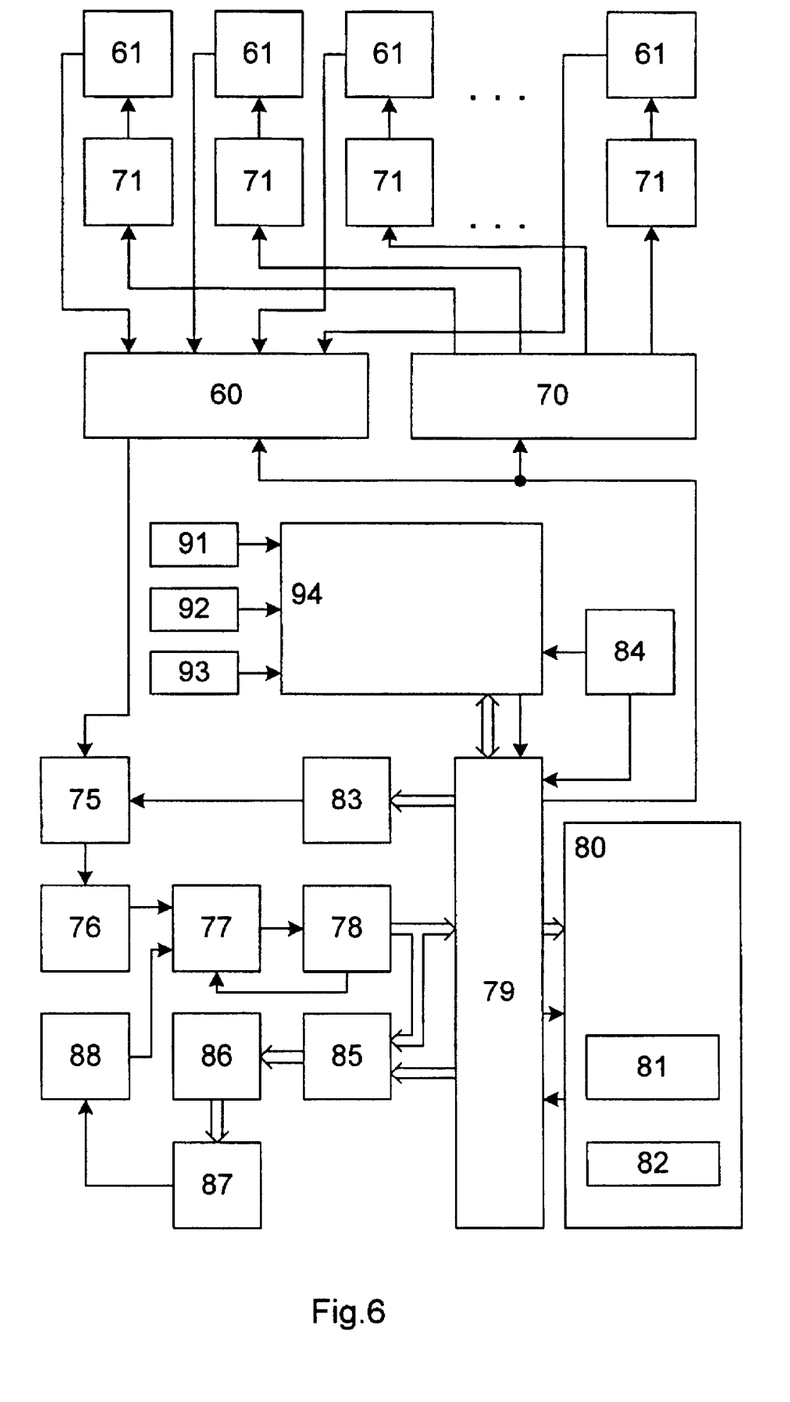
FIG. 6 is a schematic of the ultrasonic sounding, recording of the reflected ultrasonic pulses, conversion and storage of the measured data.

Referring to FIG. 6, the consecutive triggering and interrogation of ultrasonic sensors 61 excited by oscillators 71 is effected with the help of a multiplexer 70, providing consecutive triggering of the oscillator 71, and an adder 60 providing consecutive interrogation of the sensors 61. The sensor triggering signal acting on the input of the multiplexer 70 initiates the oscillator 71, which, in turn, triggers the ultrasonic sensors 61 by a 300-V voltage pulse: Besides, the sensor triggering signal acts on the control input of the adder 60 synchronizing the reception of the pulses from the sensors 61. The signal (pulse) taken from the sensors 61 is applied through the adder 60 to a controlled amplifier 75, from the output of which the pulse from the sensor passes through a logarithmic amplifier 76 to one of the inputs of an adder 77. The amplification factor of the controlled amplifier 75 is set with the help of a digital-to-analog converter 83 controlled by the module for conversion of digital data. From the output of the adder 77 the pulse is fed to the ADC 78, where the analog-to-digital conversion of the pulse amplitude is effected. The digitized amplitudes from the ADC 78 are applied to a digital data conversion module 79 and to one of the inputs of a noise level measuring circuit 85, the second input of the circuit 85 being fed with a reference voltage from the module 79 The signal from the output 85 is applied to the input of a code shaper 86 of a digital-to-analog converter 87. The analog signal from a digital-to-analog converter (DAC) 87 is fed through a low-pass filter 88 to the second input of the adder 77. The value of the lower limit of the digitization range from the output of the ADC 78 is applied to the third input of the adder 77. The digital data converted in the module 79 are applied to the onboard computer 80, where the data are recorded in a digital data storage device 81, the data being recorded in files with registration of the time of opening and closing the file by a timer 82. The timer 82 is synchronized with a clock oscillator 84.

The timing of the scan mode (emission of the probing pulses) is effected in a circuit 94 processing the odometric data fed from the odometers 91, 92, 93 (FIG. 6). The outputs of the odometers 91, 92, 93 are connected to the inputs of the circuit 94, the output of the circuit 94 used for triggering the ultrasonic sensors is connected to one of the inputs of the circuit 79 whose output used for starting the ultrasonic pulses is connected to the input of the multiplexer 70 and to the adder 60. The data determining the mode of processing the odometric data in the circuit 94 are fed from the circuit 79 to the circuit 94, the converted odometric data from the circuit 94 being applied to the circuit 79. The output of the timer 84 is also connected to one of the inputs of the circuit 94.

Figure 5:
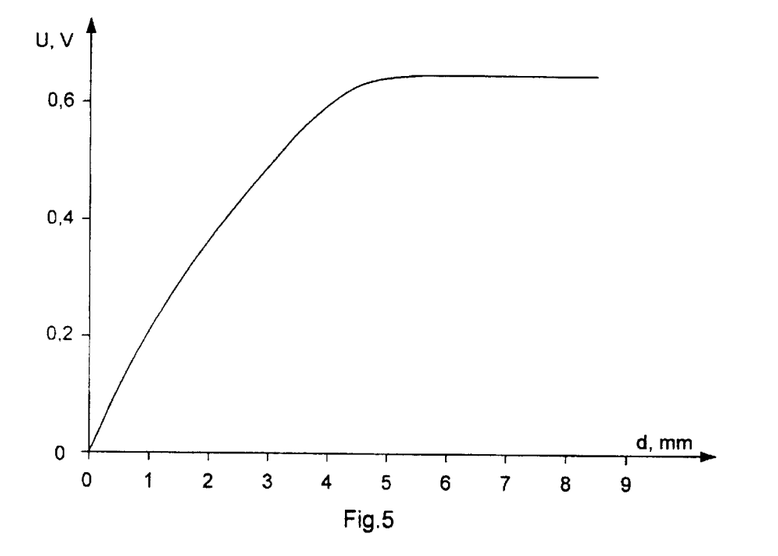
FIG. 5 illustrates the dependence of the amplitude of the electric pulse corresponding to the ultrasonic pulse reflected from the crack-like flaw on the flaw depth.

During the reflection of the ultrasonic pulse from the crack-like flaw the maximum pulse amplitude represents the crack depth. FIG. 5 illustrates the dependence of the maximum amplitude U of the electric pulse of a respective ultrasonic pulse reflected from the crack-like flaw from the flaw depth d at a preset rate of ultrasound absorption. Since the ultrasonic pulses received when testing the pipeline have a different path length and, therefore, are absorbed to a different extent, the amplitude of the electric pulses corresponding to the received ultrasonic pulses is normalized by varying the amplification factor depending on the time elapsed from the moment of emission of the probing pulse.

In a time interval from 8.4 microseconds to 56.6 microseconds, the factor K of amplification of the electric pulses transmitted from the ultrasonic sensors is increased discretely with a step of 8.4 microseconds (by 8 steps) so that the maximum value of K is about $1.5K_0$.

Figure 7:
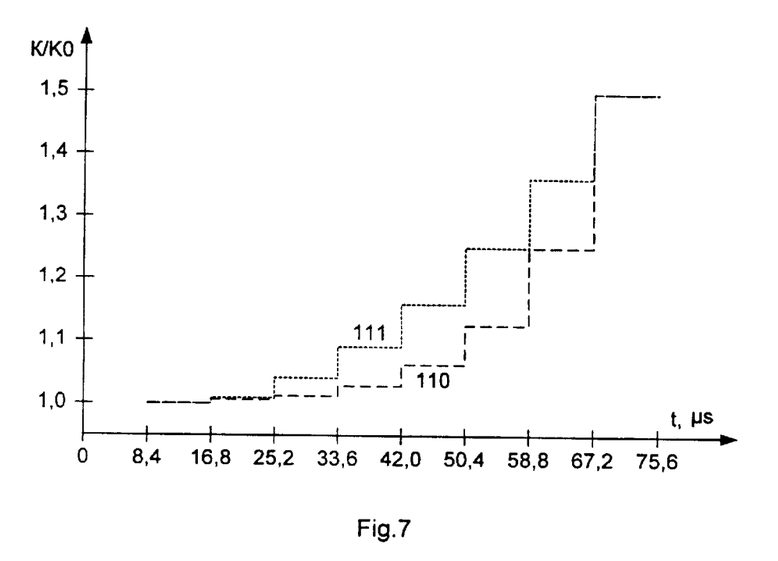
FIG. 7 illustrates the time dependence of the amplification factor of the electric pulses corresponding to the received ultrasonic pulses.

In one of the possible embodiments, the amplification factor K is increased as a function of $K=K_0(1+2^{(M-9)} \text{sgn}(M-1))$, where $K_0$ is the initial value of the amplification factor (at the 1st step), M is the step number ($M=[(t-t_0)/dt+1]$, where t=8.4 microseconds is the time elapsed after the emission of the ultrasonic probing pulse, when the amplification of the pulses is initiated; dt is the length of the time slot equal to 8.4 microseconds so that the maximum value of K is $1.5K_0$; the dependence of the amplification factor K on time t, elapsed after the emission of the probing pulse, is presented in FIG. 7 by a curve 110. In so doing the maximum variation of the amplification factor K is $0.25K_0$. Such an embodiment may be based on a simple hardware, for example, made in the form of a single counter.

In another possible embodiment the factor K of amplification of the electric pulses sent from the ultrasonic sensors is increased depending on the above time t elapsed from the moment of emission of the ultrasonic probing pulse, as an approximation function $K=c+a(t-b)^n$, wherein K is the amplification factor, t is time elapsed from the moment of emission of the ultrasonic probing pulse, a,b,c,n—are approximation variables; a is a positive value, n is not less than 1, b does not exceed the lower limit of the time interval, and c is any appropriate value. Being considerable through discrete amplification factor changing this function is transformed to the function $K=K_0(1+0.01(M-1)^2)$, M is a number of the step taken according to $M=[(t-t_0)/dt+1]$, where to is the time elapsed after the emission of the ultrasonic probing pulse, from which the amplification of the pulses is started, dt is the time slot of the step. In this case $c=K_0$, b=to , n=2, $a=0.01K_0/dt^2$, $t_0$=8.4 microseconds, dt=8.4 microseconds In so doing the maximum variation of the amplification factor K is $0.13K_0$, The dependence of the pulse amplification factor K on time t elapsed after the emission of the probing pulse is illustrated in FIG. 7 by the curve 111.

Thus the amplification factor K is increased as a function of $K=K_0(1+2^{(M-9)} \text{sgn}(M-1))$ or $K=K_0(1+0.01(M-1)^2)$.

In the preferred embodiment, the amplification of the electric pulses from the ultrasonic sensors is increased depending on the above time, elapsed from the moment of emission of the ultrasonic probing pulse, according to tabulated function of the step number. The tabulated function is determined under laboratory conditions depending on the type of fluid medium (water, oil, kerosene, diesel fuel or another product).

The threshold value is varied discretely with a step of 4.2 microseconds as a preset function of time depending on the sensor whose pulses are being processed at the given instant of time.

The dependencies of the amplification factor and threshold values on time in the process of the scanning pig travel inside the pipeline are read out from the device used for conversion and storage of digital data (onboard computer modules) and an individual dependence of the amplification factor and threshold value on time is set for each sensor With the time interval, during which the ultrasonic pulses are received from this sensor.

The initial values of the amplification factor are determined for each ultrasonic sensor before emitting the ultrasonic pulses towards the wall of the tested pipeline, exciting the ultrasonic sensor by the electric pulse at a voltage of 300 V, thereby emitting an ultrasonic pulse perpendicularly to the steel wall of a known thickness near the sensor and receiving the respective ultrasonic pulse reflected from the wall surface remote from the sensor using the same ultrasonic sensor by increasing the amplification factor by a predetermined algorithm realized by the devices for conversion and storage of the data to achieve a peak amplitude of the pulse in a range of 0.7–0.8 of the possible allowable value of the pulse amplitude (1 V). The DAC codes corresponding to the thus determined initial values of the amplification factor are recorded in the RAM of "PLIS" for pig operation and are kept in the peripheral storage device as files for future use.

For the first travel of the pig, the threshold values obtained during the technical adjustment of the pig are established. The results of the pig travel are used for determining a time zone of 4.2 microseconds after sending the probing pulse, in which the number of noise pulses is in a range of 8 to 16. If the number of noise pulses exceeds the above range, the programmed threshold value is increased for the given time zone stepwise by 4 to 5 mV. If the number of noise pulses is below the above range, the programmed threshold value is reduced for the given time zone stepwise by 4 to 5 mV. In this case the number of time zones is equal to 16. After that the digitized amplitudes of the received electric pulses are compared with the digital threshold value.

The next pig travel is performed using the found threshold values for each time zone recorded in the PLIS RAM.

In one of embodiment of the method, the above-said recorded values are corrected during the pig travel using the above described algorithm.

According to the algorithm executed following the program in the onboard computer, the measured digital values from a group of sensors are combined in data frames, each data frame including the parameters of the received pulses corresponding to the probing pulses for each ultrasonic sensor, as well as the timer time uniquely connected with the time of emission of said probing pulses. The above parameters of the received pulses include digital values of the pulse amplitude and time for each amplitude value after emitting a respective probing pulse. The above parameters of the received pulses include maximum digitized amplitudes of the pulses and time corresponding to this maximum and elapsed from the instant of emitting the respective probing pulse.

The data frame includes the above parameters of the received pulses corresponding to 64 probing pulses for each sensor of the group of ultrasonic sensors. The timer time is recorded for each said group of sensors, said time being uniquely connected with the time of triggering each sensor of the above group of sensors.

The digital data are recorded in the digital data storage device in the file 20 of said data frames. Also recorded in this device is the time of opening and closing the file, this time being determined by the computer clock controlling the data recording operation. The computer clock time and timer time are synchronized with each other and with the time of an external timer before and after the pig travel.

In the preferred embodiment of the invention during the pig travel the wall thickness and the crack-like flaws are measured. Several ultrasonic sensors (group of sensors) are triggered simultaneously through a preset time interval. The time slot between the adjacent odometric pulses corresponds to a length of about 3 millimeters measured by the odometer. During the pipe scanning operation the speed of the pig inside the pipeline is determined and the condition is observed that the pig speed must not be less than 0.1 m/s and not higher than 1.5 m/s. If this range is maintained, the ultrasonic sensors are triggered through a preset time interval.

After the inspection of a given section of the pipeline has been completed, the pig defectoscope is withdrawn from the pipeline, and the data collected during the pig travel are rewritten to the external computer.

The subsequent analysis of the recorded data allows one to detect flaws of the pipe wall and to determine their position on the pipeline for the purpose of a subsequent repair of the damaged sections of the pipeline.

Figure 8:
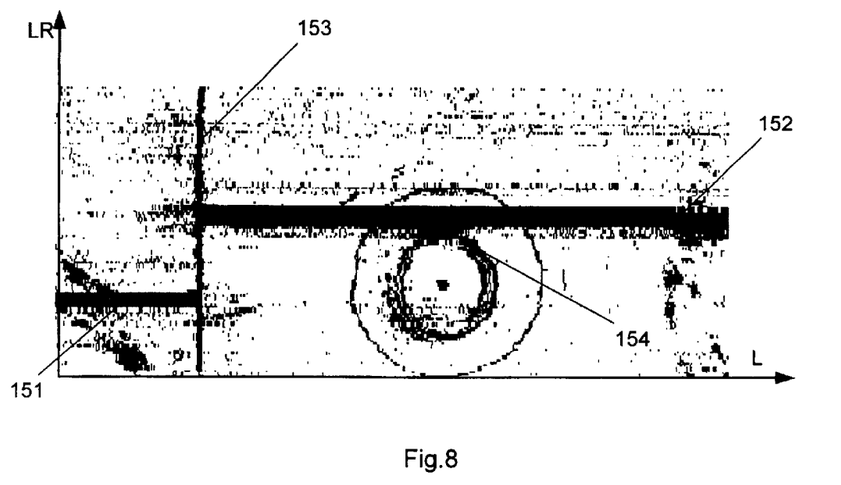
FIG. 8 is a graphic representation of the measured data on the pipe wall thickness along one section of the pipeline being tested allowing the welded joints to be identified.
Figure 9:
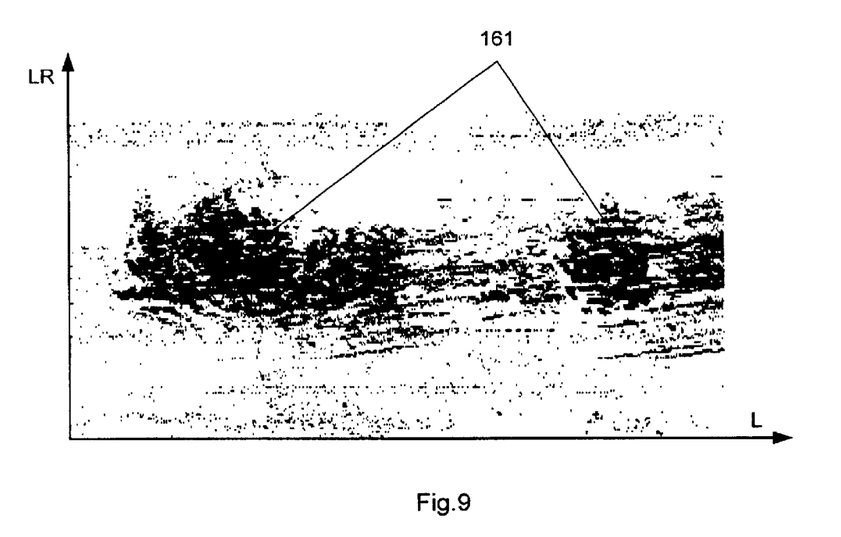
FIG. 9 is a graphic representation of the measured data on the pipe wall thickness along one section of the pipeline being tested allowing the corrosion loss of metal to be identified.

FIGS. 8 and 9 illustrate fragments of a graphic representation of the data obtained due to the diagnostic pig travel allowing the operator to define the specific features of the pipeline and the flaws of its walls. Plotted on the axis L in FIGS. 8 and 9 is the length of the pipeline along its axis and on the axis LR there is plotted the length along the perimeter in the pipeline cross section. The black dots on the image show that at these spots on the pipe the difference between the measured value of the wall thickness and the nominal value for the given section of the pipeline exceeds the preset threshold value. FIG. 8 illustrates the characteristic features of the pipelines: longitudinal welded joints 151 and 152 of the pipes, a welded joint between the pipes 153, and a plunger 154. Shown in FIG. 9 are typical corrosive flaws 161 on the pipe detected as a result of performing the in-tube ultrasonic defectoscopy by the present method.

Thus, there is provided a method of in-tube ultrasonic inspection of pipelines carried out by passing inside the pipeline a scanning pig, emitting ultrasonic probing pulses towards the pipe wall and receiving the reflected ultrasonic pulses. The method is characterized in that the received pulses are amplified using a different amplification factor, which is increased depending on the time elapsed from the moment of emitting the probing pulse. The threshold values of the pulse amplitudes are also varied depending on time. Digital values of the pulse amplitudes and the time elapsed from the moment of emitting the probing pulse and corresponding to each value of the amplitude are obtained. The empirically obtained dependencies of the amplification factor and threshold on time for each ultrasonic sensor are recorded in a RAM memory. During the processing of the received pulses, the previously recorded dependencies for each ultrasonic sensor are readout from the RAM and the respective values of the amplification factor and threshold are established simultaneously with a period, during which the pulses are received with the help of this sensor. The method allows one to hardwarily compensate the effect of ultrasound attenuation in the material on the amplitudes of the reflected pulses and, in this manner, to increase the accuracy of determining the geometrical parameters of the flaws, a probability of their detection and efficiency of estimation of their danger.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method of in-tube ultrasonic inspection of a pipeline by passing inside the pipeline a scanning pig including ultrasonic sensors, means for measuring data, means for processing measured data, and means for storing measured data during travel of the pig, the method comprising:

emitting ultrasonic probing pulses from the sensors;

receiving at the sensors reflected ultrasonic pulses corresponding to each of the ultrasonic probing pulses;

amplifying electric pulses from the sensors corresponding to the received reflected ultrasonic pulses; and comparing amplitude values of the electric pulses corresponding to the received reflected ultrasonic pulses to a threshold value, wherein an amplification factor for the electric pulses from the sensors and the threshold value are varied discretely as a function of time within a time interval following emission of each ultrasonic probing pulse, wherein a lower limit of the time interval is in the range of 3–20 microseconds, and an upper limit of the time interval is in the range of 40–200 microseconds, and wherein the amplification factor is increased depending on time elapsed from emission of the ultrasonic probing pulse in accordance with the function $K=c+a(t-b)^n$ wherein K is the amplification factor, a is a positive value, n is not less than 1, t is time elapsed from the moment of emission of the ultrasonic probing pulse, b does not exceed the lower limit of the time interval, and c is any appropriate value.

2. A method according to claim 1, wherein n=2.

3. A method according to claim 1, wherein the amplification factor is varied discretely with a period of 2 to 20 microseconds and with a maximum step of 0.25 times an initial value of the amplification factor.

4. A method according to claim 1, wherein the threshold value is set discretely with a period of 1–10 microseconds and wherein the threshold value is digitized and digitized amplitude values of the electric pulses are compared with the digitized threshold value.

5. A method according to claim 1, wherein:

the time interval is divided into several time zones after emission of each probing pulse, false pulses are counted in each zone, a threshold value for each zone is set depending on the number of false pulses exceeding a threshold value in the respective zone for several probing pulses, the number of time zones is not less than 4 and is not more than 128, and the threshold value is set dependent on time in which one ultrasonic probing pulse corresponds to 8 to 16 received false pulses exceeding the threshold value at the time of recording of the false pulses.

6. A method according to claim 5, wherein:

the number of false pulses is determined after completing one travel of the pig, the dependence of the threshold value on time being set for a subsequent diagnostic pig travel, and the false pulses are noise pulses.

7. A method according to claim 1, wherein the threshold value is digitized and digitized amplitude values of the electric pulses are compared with the digitized threshold value, and digitized parameters of the electric pulses are combined into data frames, the parameters including digitized amplitudes of the electric pulses and time elapsed after emitting the corresponding probing pulse, each data frame including parameters of electric pulses corresponding to 10 to 1000 probing pulses for each sensor, for each sensor, an operating time is determined by a timer in the pig and recorded, the operating time being uniquely matched with a time of triggering each sensor, and a file of a plurality of the data frames and a time of opening and closing the file is stored in the means for storing measured data, the time of opening and closing the file being determined by a clock of the means for storing measured data, the clock and the timer in the pig being synchronized with each other and with the time of another timer located beyond the pig.

8. A method of in-tube ultrasonic inspection of a pipeline by passing inside the pipeline a scanning pig including ultrasonic sensors, means for measuring data, means for processing measured data, and means for storing measured data during travel of the pig, the method comprising:

emitting ultrasonic probing pulses from the sensors;

receiving at the sensors reflected ultrasonic pulses corresponding to each of the ultrasonic probing pulses;

amplifying electric pulses from the sensors corresponding to the received reflected ultrasonic pulses; and comparing amplitude values of the electric pulses corresponding to the received reflected ultrasonic pulses to a threshold value, wherein an amplification factor for the electric pulses from the sensors and the threshold value are varied discretely as a function of time within a time interval following emission of each ultrasonic probing pulse, and wherein the amplification factor of the electric pulses received from the ultrasonic sensors is increased stepwise depending on time elapsed from emission of the ultrasonic probing pulse in accordance with the function $K=K_0(1+a*2^{M-N})$ wherein K is the amplification factor, M is the step number, N is the maximum number of steps, $K_0$ is the initial value of the amplification factor, a is a positive value, and N is not less than 6.

9. A method according to claim 8, wherein:

a lower limit of the time interval is in the range of 3–20 microseconds, and an upper limit of the time interval is in the range of 40–200 microseconds, and the amplification factor is varied discretely with a period of 2 to 20 microseconds and with a maximum step of 0.25 times an initial value of the amplification factor.

10. A method according to claim 8, wherein:

a lower limit of the time interval Is In the range of 3–20 microseconds, and an upper limit of the time interval is in the range of 40–200 microseconds, the threshold value is set discretely with a period of 1–10 microseconds, and the threshold value is digitized and digitized amplitude values of the electric pulses are compared with the digitized threshold value.

11. A method according to claim 8, wherein:

the time interval is divided into several time zones after emission of each probing pulse, false pulses are counted in each zone, a threshold value for each zone is set depending on the number of false pulses exceeding a threshold value in the respective zone for several probing pulses, the number of time zones is not less than 4 and is not more than 128, and the threshold value is set dependent on time in which one ultrasonic probing pulse corresponds to 8 to 16 received false pulses exceeding the threshold value at the time of recording of the false pulses.

12. A method according to claim 11, wherein:

the number of false pulses is determined after completing one travel of the pig, the dependence of the threshold value on time being set for a subsequent diagnostic pig travel, and the false pulses are noise pulses.

13. A method according to claim 8, wherein the threshold value is digitized and digitized amplitude values of the electric pulses are compared with the digitized threshold value, and digitized parameters of the electric pulses are combined into data frames, the parameters including digitized amplitudes of the electric pulses and time elapsed after emitting the corresponding probing pulse, each data frame including parameters of electric pulses corresponding to 10 to 1000 probing pulses for each sensor, for each sensor, an operating time is determined by a timer in the pig and recorded, the operating time being uniquely matched with a time of triggering each sensor, and a file of a plurality of the data frames and a time of opening and closing the file is stored in the means for storing measured data, the time of opening and closing the file being determined by a clock of the means for storing measured data, the clock and the timer in the pig being synchronized with each other and with the time of another timer located beyond the pig.

* * * * *